United States Patent
Lalonde et al.

(10) Patent No.: US 6,270,493 B1
(45) Date of Patent: Aug. 7, 2001

(54) CRYOABLATION STRUCTURE

(75) Inventors: Jean-Pierre Lalonde; Cristian Petre; Robert Martin, all of Québec; Claudia Lueckge, Quebec; Sean Carroll; Dan Wittenberger, both of Québec; George Klein, London, all of (CA)

(73) Assignee: CryoCath Technologies, Inc., Kirkland (CA)

(*) Notice: Subject to any disclaimer, the term of this patent is extended or adjusted under 35 U.S.C. 154(b) by 0 days.

(21) Appl. No.: 09/356,433

(22) Filed: Jul. 19, 1999

(51) Int. Cl.[7] .................................................. A61B 18/18
(52) U.S. Cl. ............................................. 606/23; 606/24
(58) Field of Search ............................................ 606/20–26

(56) References Cited

U.S. PATENT DOCUMENTS

| | | |
|---|---|---|
| 3,425,419 | 2/1969 | Dato . |
| 3,859,986 | 1/1975 | Okada et al. . |
| 3,948,269 | 4/1976 | Zimmer . |
| 4,946,460 | 8/1990 | Merry et al. . |
| 5,078,713 | 1/1992 | Varney . |
| 5,211,646 * | 5/1993 | Alperovich et al. ................ 606/23 |
| 5,254,116 | 10/1993 | Baust et al. . |
| 5,275,595 | 1/1994 | Dobak, III . |
| 5,281,213 | 1/1994 | Milder et al. . |
| 5,281,215 | 1/1994 | Milder et al. . |
| 5,324,286 | 6/1994 | Fowle . |
| 5,403,309 | 4/1995 | Coleman et al. . |
| 5,423,807 * | 6/1995 | Milder ................................ 606/20 |
| 5,520,682 | 5/1996 | Baust et al. . |
| 5,573,532 | 11/1996 | Chang et al. . |
| 5,624,392 | 4/1997 | Saab . |
| 5,716,353 | 2/1998 | Matsuura et al. . |
| 5,759,182 | 6/1998 | Varney et al. . |
| 5,800,487 | 9/1998 | Mikus et al. . |
| 5,800,488 | 9/1998 | Crockett . |
| 5,833,685 | 11/1998 | Tortal et al. . |
| 5,860,970 | 1/1999 | Goddard et al. . |
| 5,860,971 * | 1/1999 | Clarke ................................. 606/24 |
| 5,902,299 * | 5/1999 | Jayaraman ........................... 606/20 |
| 5,971,979 * | 10/1999 | Joye et al. ........................... 606/21 |

* cited by examiner

*Primary Examiner*—Michael Peffley
(74) *Attorney, Agent, or Firm*—Gunster, Yoakley & Stewart, P.A.

(57) ABSTRACT

A cryocatheter for treatment of tissue includes a coolant line communicating with a cryochamber having a coolant receiving interior and a thermally conductive wall for contacting and conductively treating tissue. A return line returns spent coolant, and an insert or partition in the cryochamber conditions flow or channels fluid from the coolant line to the return line to enhance the rate or uniformity of cooling. The partition may extend axially to define an elongated sub-chamber which is preferentially cooled, or it may isolate one side to define an uncooled side of the cryochamber. The partition may extend axially to define a sub-chamber extending along a segmented length around a partial circumference of the catheter tip, or may channel the coolant from a central region outwardly against the peripheral wall of the cryochamber. The return line may be a vacuum return line. The catheter may include a means for warming the catheter tip to warm up or accelerate thawing of treated tissue, and the heating may be implemented by a heater in thermal contact with a fluid supply line, which may, moreover, be the coolant supply line. Alternatively, the warming fluid supply line may be distinct from the coolant line. In one embodiment, the device may connect the warming line as an additional coolant return line during cryotreatment, and switch its connection to supply warming fluid after the tissue has been cooled. The catheter may further include sensors such as thermal or impedance sensors for sensing contact orientation of the catheter against adjacent tissue. Electrodes may apply signals of two different frequencies to the two sides, and a processor may determine frequency, impedance or a differential temperature to indicate the tip contact orientation.

19 Claims, 5 Drawing Sheets

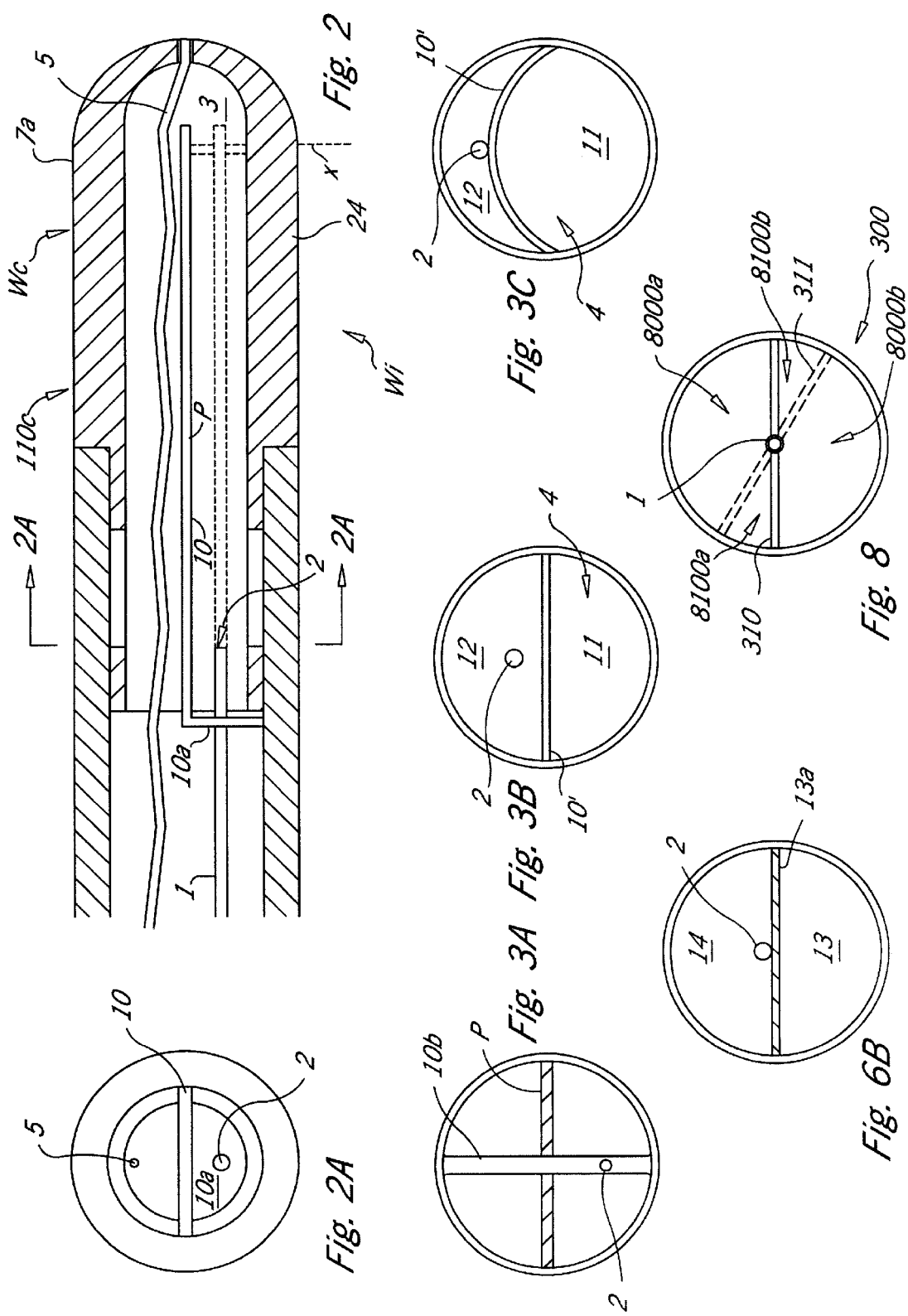

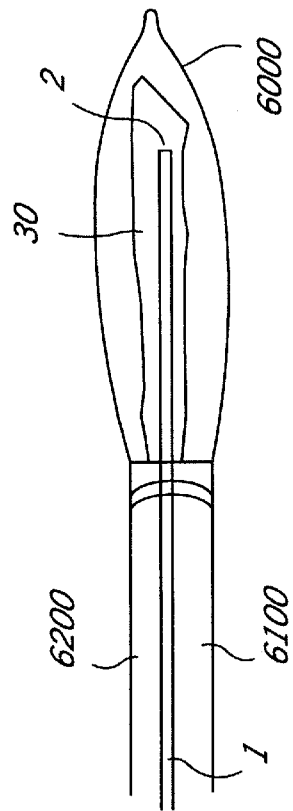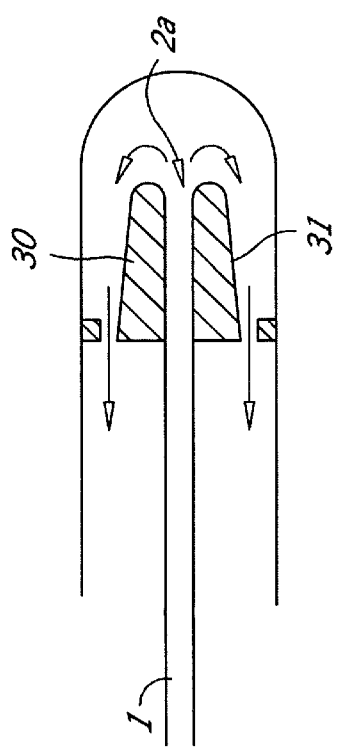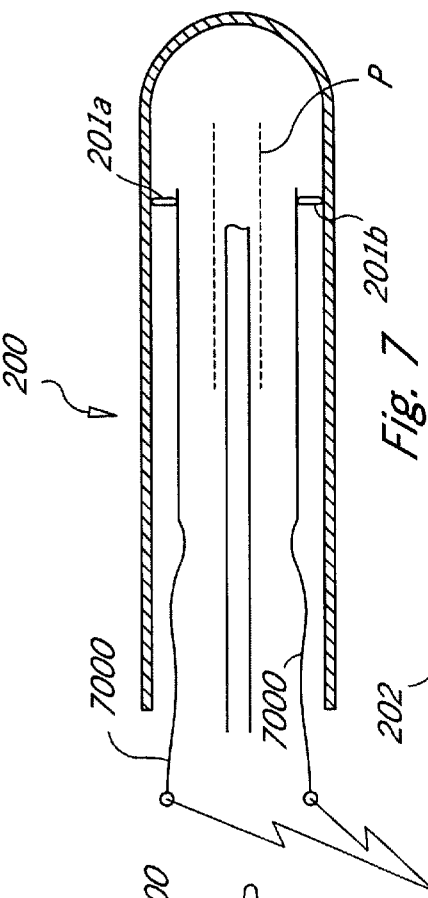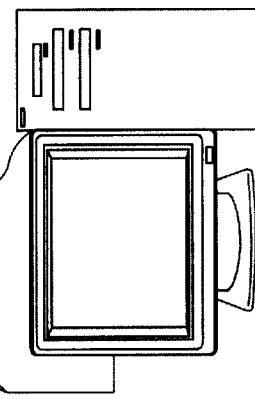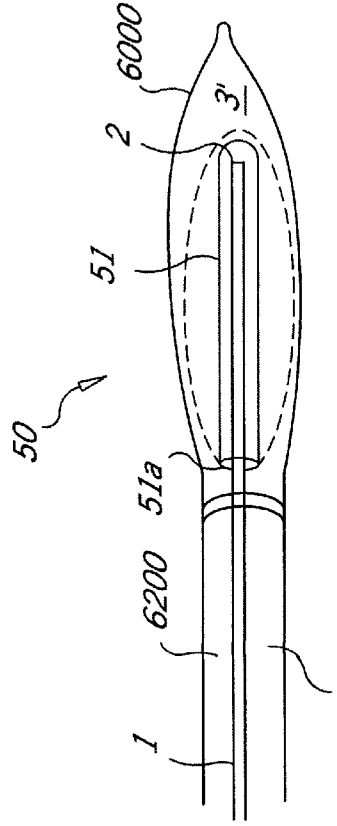
Fig. 5
Fig. 6
Fig. 6A
Fig. 7

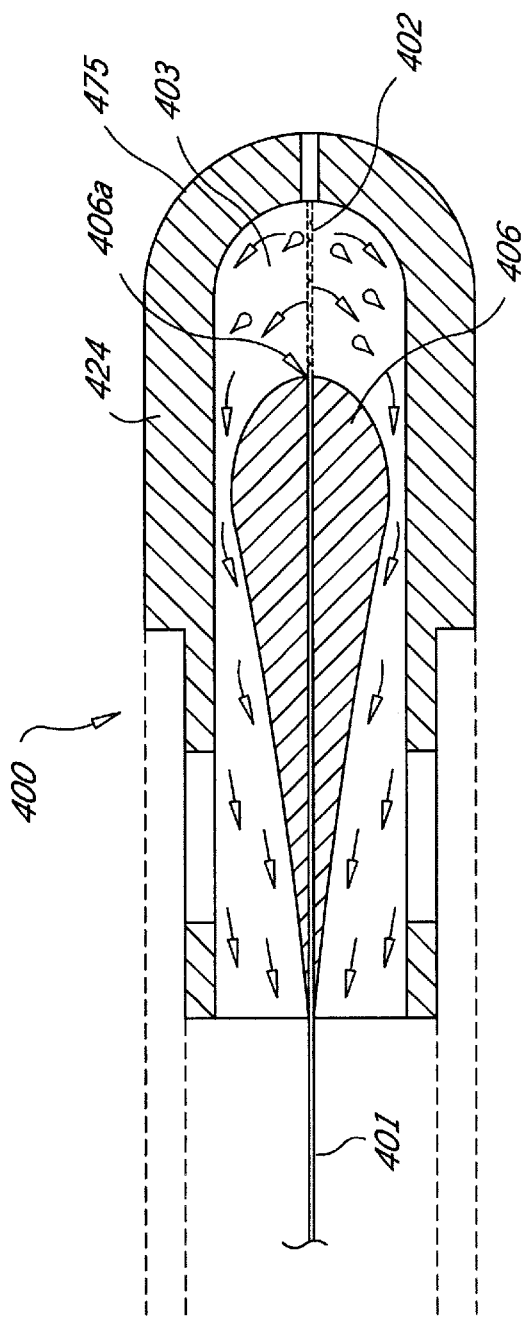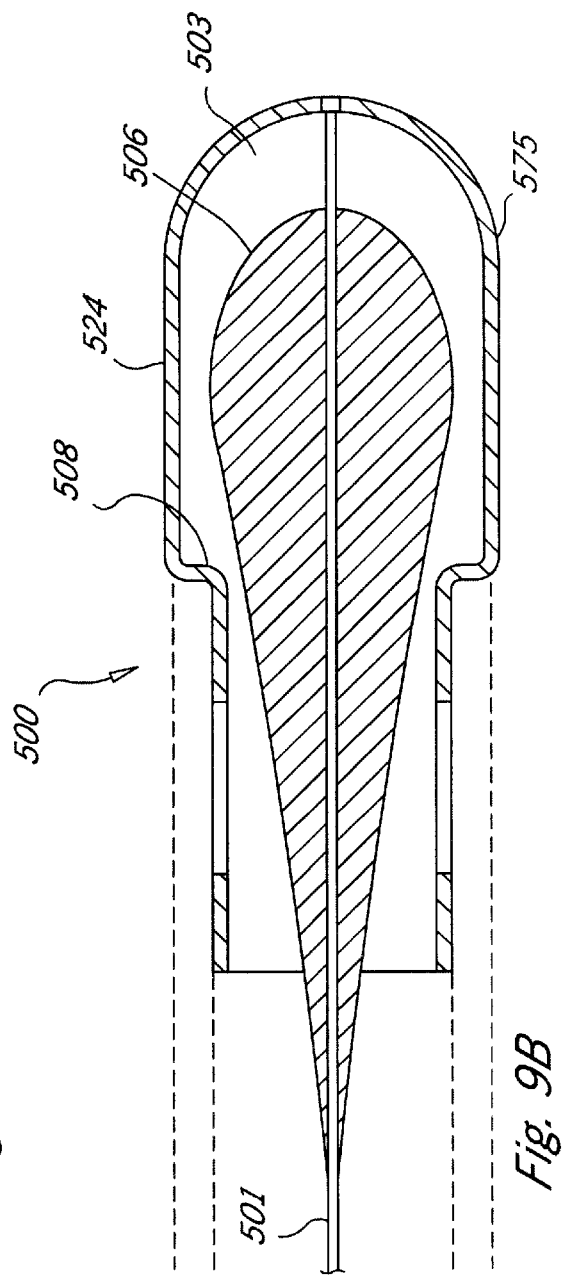

CRYOABLATION STRUCTURE

CROSS-REFERENCE TO RELATED APPLICATIONS

Not applicable.

STATEMENT REGARDING FEDERALLY SPONSORED RESEARCH

Not applicable.

FIELD OF THE INVENTION

The present application relates to cryocatheters and wands, i.e. to catheters and wands which are used to treat tissue by cooling contact. Such implements, henceforth generically referred to herein as "cryocatheters" or simply "catheters" have an elongated body through which a cooling fluid circulates to a tip portion which is adapted to contact and cool tissue. In general, cooling catheters may be used to lower the temperature of tissue, such as cardiac wall tissue, to an extent such that signal generation or conduction ceases and allows one to map or confirm that the catheter is positioned at a particular lesion or arrhythmia conduction site. More recently, cryocatheters have been configured for ablation treatment, to cool the tissue to a much lower level at which freezing destroys the viability of the tissue, and, in the case of cardiac tissue, permanently removes it as a signal generating or signal conducting locus. Such devices are also useful for tissue destruction in other contexts, such as the ablation of tumorous, diseased, precancerous or congenitally abnormal tissue.

Cryocatheters may be adapted for endovascular insertion, or for insertion along relatively confined pathways, for example through a body lumen, or through a small incision to and around intervening organs, to reach an intended ablation site. As such, they are characterized by a relatively elongated body through which the cooling fluid must circulate, and a tip or distal end portion where the cooling is to be applied. The requirement that the coolant be localized in its activity poses stringent constraints on a working device. For example when the catheter contact must chill tissue to below freezing, the coolant itself must attain a substantially lower temperature. Furthermore the rate of cooling is limited by the ability to supply coolant and circulate it through the active contact region, and the efficacy of the contact region itself is further limited by geometry and physical properties that affect its ability to conduct heat into the tissue. The rate of cooling may change depending upon the effectiveness of thermal contact, e.g. upon the contact area and contact pressure between the catheter and the tissue, and may be further influenced by ice accumulations or other artifacts or changes due to the freezing process itself. Moreover, it is a matter of some concern that proximal, adjacent or unintended tissue sites should not be exposed to harmful cryogenic conditions. These somewhat conflicting requirements make the actual implementation of an effective cryocatheter complex.

One approach has been to provide a phase change coolant which is pumped as a liquid to the tip of the catheter and undergoes its phase change in a small chamber located at the tip. The wall of the chamber contacts adjacent tissue directly to effect the cooling or ablation treatment. Such a device can treat or achieve a relatively high rate of heat energy transfer. Moreover, by employing a phase change refrigerant which may be injected at ambient temperature along the body of the catheter and undergo expansion at the tip, the cooling effect may be restricted to the localized treatment region surrounding the tip portion of the device. The dimensions of catheter construction, particularly for an endovascular catheter, require that the phase change coolant be released from a nozzle or tube opening at a relatively high pressure, into a relatively small distal chamber of the catheter. After the fluid expands in the distal chamber and cools the walls, it is returned through the body of the catheter to a coolant collection system, preferably in the form of a recirculation loop.

However, the high pressure release of coolant in a relatively small chamber at the tip of the catheter and its recirculation back via a return conduit from the tip region involve relatively turbulent fluid flow conditions, so that the precise rate of heat transfer that occurs may be subject to rather wide variations. For cardiac ablation, the injection is controlled from a low rate of delivery for cold mapping or treatment site confirmation, to a higher rate of delivery used for tissue ablation at the mapped or confirmed sites. For other applications such as thermal angioplasty, proper treatment may require precise control of the cooling in other temperature ranges. The wide range of required energy transfer rates as well as differences in size, shape or construction of different catheters increases the difficulty of achieving uniform or repeatable catheter cooling rates. This in turn has resulted in instruments that operate in restricted temperature ranges and with wide variations in their cooling characteristics.

Accordingly, there remains a need for a cryocatheter tip construction that more effectively controls the flow of thermal transfer fluid.

There is also a need for a cryocatheter construction that ablates tissue more effectively, or in shorter times.

There is further a need for a cryocatheter construction, which is controllable to provide uniform and repeatable cooling over a range of thermal energy transfer rates.

SUMMARY OF THE INVENTION

One or more of the foregoing desirable objects are achieved in accordance with the present invention by a cryocatheter for treatment of tissue wherein a coolant line communicates with a cryochamber having a coolant receiving interior and a thermally conductive wall for contacting and conductively treating tissue. A return line returns spent coolant, and a body in the chamber controls or conditions the coolant flow. This may be a partition in the cryochamber that channels or directs the fluid as it enters via the coolant line to enhance the cooling efficacy. The partition may be configured to reduce fluctuations and produce a regular flow such that cooling regimens are dependably achieved without substantial variation when directly controlling only one or a few variables, such as coolant injection pressure, cycle time or the like. In various embodiments, the partition may extend axially to define an elongated sub-chamber of the tip interior that is preferentially cooled, and/or it may isolate one side of the tip to define an inert or uncooled side of the cryochamber. The partition may also be configured to define a flow or expansion sub-chamber that extends along a segmented length around a partial circumference of the catheter tip, or may be configured to channel the coolant from a central region outwardly against the peripheral wall of the cryochamber. The body may also be a shaped flow conditioner that controls the flow path and flow characteristics to the return port. Preferably, the return line is a vacuum return line. In another embodiment, the catheter includes a fluid warming provision for warming the catheter tip to heat the treated tissue. The catheter then operates to remove and to supply heat energy so as to effect a freeze/thaw or a cool/warm regimen for tissue ablation or mapping. This heating may be implemented by a heater in thermal contact with a fluid supply line, which may be either the coolant supply line or a separate line that carries a separate warming fluid. In one embodiment of this aspect, a switching valve connects a warming fluid supply passage such that the passage functions as an additional return line during application of coolant to the cryochamber, and the valve switches its connection at the start of a warming cycle to supply warming fluid in a reverse direction of flow through that line to the tip after the tissue has been cooled. The catheter may further include sensors for sensing contact orientation of the cooling tip against adjacent tissue. Such sensors may include a first impedance sensing electrode on a first side of the cryochamber, and a second impedance sensing electrode on a second side of the cryochamber, which operate in conjunction with one or more body surface electrodes to define a determinable sensing path or otherwise indicate which side of the cryochamber is in contact with tissue at a given time. The impedance sensing electrodes may apply signals of different frequency at opposite sides of the tip to facilitate the determination of tip contact surface orientation. Temperature sensors may also be used, such as a first temperature sensor on one side of the cryochamber and a second temperature sensor on another side of the cryochamber. In that case, the temperature sensor electrical outputs extend through the catheter body to a console and their respective signals are processed to show a differential temperature or other indication from which the device determines the orientation or tissue-contacting side of the tip.

BRIEF DESCRIPTION OF THE DRAWINGS

These and other features of the invention will be understood from the description of illustrative embodiments and the operation thereof, taken together with the drawings of representative embodiments, wherein:

FIG. 2 schematically illustrates one embodiment of the present invention;

FIG. 2A shows an axial view from the proximal end of the embodiment of FIG. 2;

FIGS. 3A, 3B and 3C show end views of three representative physical embodiments of a catheter in accordance with the present invention;

FIG. 5 illustrates a radially configured flow embodiment;

FIGS. 6, 6A illustrate a heat/cool embodiment;

FIG. 6B illustrates an embodiment having a buffer region;

FIG. 7 illustrates orientation sensing of any of the foregoing embodiments;

FIG. 8 illustrates a divider membrane embodiment; and

FIGS. 9A and 9B illustrate two constructions of an embodiment with a flow conditioning body in the cooling chamber.

DETAILED DESCRIPTION OF THE DRAWINGS

Figure 1:
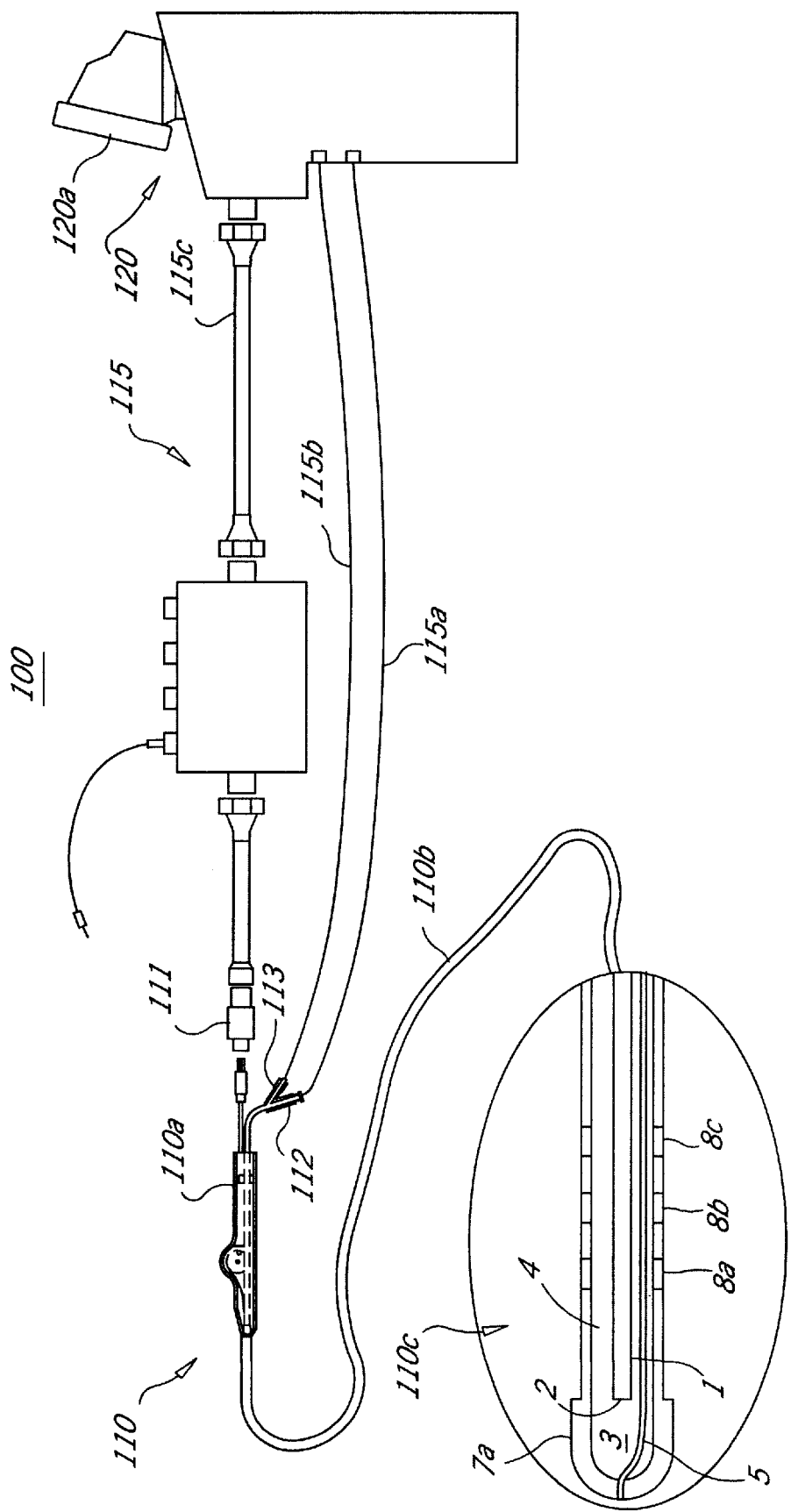
FIG. 1 shows a cryoablation system generally representative of both the prior art and the present invention.

FIG. 1 shows a cryogenic treatment system 100 illustrating representative elements thereof. System 100 includes a treatment catheter 110 having a handle 110a, and elongated cryogen transporting body 110b and a catheter tip 110c. The catheter 110 is connected by various conduits or cables to a console 120 which may, for example, have a display monitor 120a and other data entry or display accessories such as a keyboard, a printer and the like. The console 120 is connected to the catheter by various lines 115 which may include a coolant injection line 115a, a coolant return line 115b, and electrical cabling 115c which carries outputs of various cardiac sensing, thermal sensing, mapping or other elements as may be used for catheter treatment or monitoring. As shown, the handle 110a is equipped with input ports for an electrical connector 111, a coolant injection tube connector 112, and a return tube connector 113. These connect by various internal junctions or tubes passing through the handle and elongated body 110b to the distal tip of the catheter. The handle may also include various control assemblies, e.g., switches or valves, as well a safety detection or shutdown elements (not illustrated).

As shown schematically in FIG. 1, the coolant is carried to the tip through a tube 1 and enters a chamber 3 at the end of the catheter tip 110c via a nozzle 2 at the end of the tube to expand in a small contained region forming the active region of the tip of the catheter. By way of example, the tube 1 may run concentrically within the elongated body 110b, and the portion of the body lumen outside of tube 1 may form a return passage for spent coolant. The tube 1 runs to the tip of the catheter where coolant exits from an orifice 2 at the end of the tube and returns through the annular space surrounding tube 1, to the fluid return connector 113 of the handle. Preferably the return passage for expended coolant is a vacuum passage, thus assuring that leakage out of the catheter into the bloodstream does not occur.

In the illustrated embodiment, the chamber, in which coolant is released from the nozzle 2 and returns to the return passage via annular opening 4, defines the cooling region of the catheter tip. This chamber may be short, less than a few centimeters long, and located at the very tip of the catheter or slightly proximal thereto. A thermocouple 5 and one or more ring electrodes 8a, 8b, 8c (FIG. 1) may be positioned at the catheter tip for performing sensing and monitoring functions.

While the foregoing description describes a cryoablation catheter system in general terms with several elements which are or may be useful in such a system, applicant specifically contemplates a cryoablation system wherein a phase change coolant is injected through the coolant line 1 to expand in the chamber 3 at the tip of the catheter, and return via a vacuum or suction passage to the return connection 113 at the catheter handle. In a system of this type developed by the assignee of the present invention, the phase change material is provided at ambient temperature but relatively high pressure through the handle and body 110a, 110b of the catheter, such that cooling only occurs upon release of pressure and expansion within the chamber 3 at the tip of the catheter. Operation of this device involves controlling the timing and amount of coolant injected through the inlet tube 1 at the injection pressure, which may, for example, be a pressure of about 400 psig. The entire catheter is dimensioned to fit in a No. 9 French introducer or smaller.

The small dimensions of this assembly have the result that flow conditions existing within the catheter tip are turbulent and chaotic. Thus, while this arrangement has been found to provide a high level of cooling, the introduction at high pressure into the small expansion chamber results in cavitation, turbulence and irregular fluid flow evolving in the short distance and brief time between the jet spray of expanding coolant and the lower pressure conditions existing at the proximal end of the chamber adjacent the coolant return passage.

In accordance with a principle aspect of the present invention, cooling flow is enhanced by placing a plate or partition or other body within the catheter chamber 3 to condition flow from the coolant inlet or nozzle, to the coolant outlet or vacuum return passage.

FIG. 2 is a schematic illustration of the invention. As shown, a bullet-shaped cap such as a machined metal end piece 7a forms a continuous wall 24 defining a closed tip of the cooling chamber. Within the catheter tip 110c a plate P is positioned to condition flow of the coolant leaving the orifice 2 of the injection tube 1. The presence of the plate serves to direct or define the flow of the fluid entering the chamber. As illustrated in end view in FIG. 2A the plate P may lie adjacent to the nozzle 2 along the direction of fluid ejection to provide a bounding surface or boundary condition for guiding, smoothing or otherwise conditioning the flow. The plate then acts to reduce fluctuations in cooling which would otherwise occur due to the irregular or transient formation or movement of drops, bubbles, conflicting flow paths and the like in the flowing, expanding coolant. Beyond its function of conditioning flow, the plate P may be positioned as a flow director, or may operate together with another surface as a flow barrier so as to define a subregion of the chamber which is preferentially cooled, thus concentrating the cooling power of the fluid stream in a smaller region. As shown in FIGS. 2 and 2A, the plate is formed as a partition or subdivider 10 in the form of a thin wall which preferably extends entirely from side to side to divide the tip interior, and is supported in part by a cross-wall which rises from the lower circumference (as shown). The cross-wall 10a may operate as a barrier defining the proximal inlet of the chamber 3 and blocking access to the vacuum return lumen at that position so that the cryofluid is made to circulate unidirectionally parallel to and around the end of the partition 10 in its flow to reach the vacuum return opening. This wall 10a may also be located closer to the distal end, e.g., at the position marked x near the end wall of the tip, with the inlet 2 extending to that point so that together with partition P it closes off a subregion and defines an inert side $W_i$ positioned so that all coolant from the tube is directed toward the other side or remaining portion $W_c$ of the interior and its wall portion is preferentially cooled. In this case, the partition 10 isolates the entire lower (as shown) region of the wall to prevent it from being subjected to thermal cooling, and more effectively channels all coolant to the small end chamber 3 and upper side $W_c$.

As shown in FIG. 3A, the inlet tube 1 need not pass through a blocking wall 10a but may be positioned by a cross bar 10b. The bar 10b does not obstruct the available vacuum return path, and allows the partition 10, blocking support 10a (if one is used) and outlet 2 to each be positioned independently of the other.

FIGS. 3B and 3C illustrate other embodiments, in which an internal partition 10' operates to condition flow for enhancing cooling of the external surface region of the catheter tip. As shown in these Figures, the partition 10' substantially bisects into two partial chambers 11, 12, and the inlet nozzle 2 is positioned in one chamber 12 while the vacuum return outlet 4 opens into the other partial chamber 11. Coolant thus circulates along the length of the tip on one side of the partition 10', around the end of the partition and along back to the vacuum outlet 4, thus being channeled to run against the internal perimeter surface of the catheter tip wall. In this manner flow is made unidirectional and relatively smooth, while being urged outwardly to the peripheral region against the wall. In the embodiment of FIG. 3C, a curved partition 10' serves to define first chamber which is thin but of large surface area and experiences a high rate of flow of cryofluid against its wall, while increasing the area of vacuum return entry on the other side of the partition. Such partitions may be advantageously formed of a membrane divider or a thin plate.

Figure 4A:
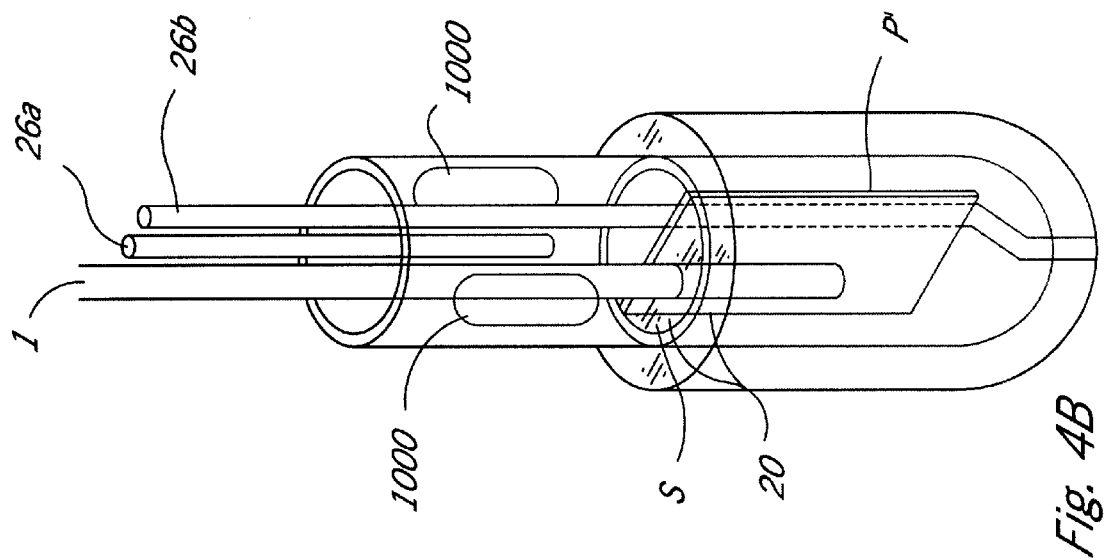
FIGS. 4A and 4B show perspective views implementing particular embodiments of the invention.
Figure 4B:
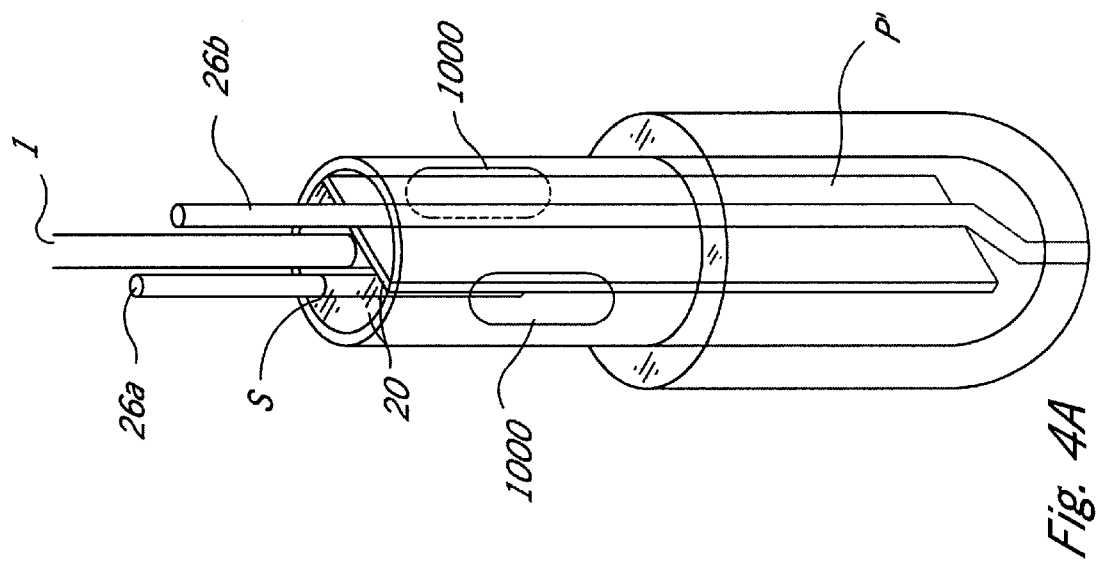

FIGS. 4A and 4B illustrate embodiments with a tip construction similar to that of FIG. 2. FIG. 2 illustrates a cross section along the longitudinal direction of a catheter tip, showing a tubular catheter body forming the major part of the catheter tip assembly, and a separate bullet-shaped tip portion 24 formed as a shell piece that closes the end and provides the expansion chamber 3 (FIG. 1). In this embodiment, the separation plate 10 extends for the length of the chamber 3, and the injection tube 1 enters along one side so that its output is confined by the separation plate 10' to run along the lower wall of the chamber. In the upper portion of the chamber a thermocouple wire extends to and is anchored at the tip of the device. The coolant having passed through the lower chamber, flows around the plate 10' through the upper chamber, so that all flow has been directed along an elongated path running against the peripheral wall of the catheter tip region. As shown in that Figure, this construction is readily implemented by assembly of the separate components together to form a closed tip catheter chamber. The overall cross-sectional area is substantially less than a square centimeter, and the tip assembled in this manner may achieve a flow chamber construction of precise dimension and flow characteristics while being made of conventional polymer materials with ample safety margin to withstand the pressure and temperature cycles involved in its operation.

FIGS. 4A and 4B show perspective views of a two tip assemblies similar to that of FIG. 2 in two alternate constructions, illustrating different locations for the divider plate to restrict the coolant region to a greater or lesser sub-portion along the length of the catheter tip. In addition to the injection tube 1, these Figures further illustrate internal cables or wires 26a, 26b which may be mechanical pull wires for steering or control, or electrical wires, for example, for temperature or other sensing operations. As illustrated, these are seated in side recesses 1000 in a molded tip piece; more than two such recesses may be provided to accommodate both steering and sensing cabling at different axial or radial positions.

In each of these embodiments, the plate 20 (FIG. 4A) or 20' (FIG. 4B) is formed as an "L" or bracket shaped insertion piece, with an elongated partition portion P' extending along the axial direction, and a cross-support or end face S securing and positioning the plate in the chamber. As shown, the injection tube passes through the support S to be positioned on one side of the plate. The support S leaves a partial circumference of the chamber open, to serve as the coolant return port from the downstream sub-chamber and define the direction of flow through the chamber. Thus, as illustrated in the foregoing embodiments, the partition within the expansion chamber may serve simply to condition flow, may limit flow to a particular subregion of the catheter tip, or may actively direct the flow against the peripheral wall of the catheter to enhance cooling in a portion or in the entirety of the tip wall, thus tailoring or improving one or more of the heat transfer contact surface or rate, the uniformity and the repeatability of cooling regimens.

The invention also contemplates that in addition to a membrane or plate serving as the flow enhancement surface, cooling may be enhanced by shaped or contoured surfaces that channel the coolant or eliminate turbulence without reducing the active cooled surface area of the tip. One such embodiment is illustrated by the flow director 30 of FIG. 5. This embodiment possesses an outer surface 31 which is generally cylindrical or frusto-conical in shape, and serves to direct flow against the catheter tip wall. the surface 31 may possess spiral ridges or flutes to smooth the flow and prevent turbulence as the entering coolant stream expands outwardly and assumes a flow direction back toward the vacuum return line formed by the catheter body lumen. Furthermore, the outer surface 31 of the flow director 30 may curve inwardly to form a nozzle 2a which initiates and smooths the influx of coolant from tube 1 along the path to the vacuum return openings.

The flow conditioner may take other forms, and may have a shape and position configured to both direct and smooth the flow of coolant. FIGS. 9A and 9B illustrate such a flow conditioning body in two different catheters 400, 500, respectively.

FIG. 9A shows a flow director body 406 having the form of a tear-drop shaped insert fastened about the coolant injection tube 401. Body 406 may be formed of any suitable material compatible with the refrigerant, and may be fastened by bonding, soldering, welding or molding it to the injection tube. The tube 401 may extend only into the central passage of body 406, so that the refrigerant exits from the distal orifice 406a of the body 406, or the tube 401 may extend distally beyond the end of the insert 406 and possess a perforated delivery section 402 which emits the refrigerant into an expansion region at the distal tip interior.

As illustrated schematically by flow field arrows, the flow in the distal expansion chamber is turbulent, and the curved distal face of the body 406 serves to channel the expanded refrigerant through a narrow passage at the inner wall of the conductive tip assembly. The insert has an aerodynamic shape that causes an increase in the velocity of the vaporizing refrigerant flowing proximally, and forces it to stay in contact with the tip wall. At the same time the turbulent flow generated by the sudden expansion of the refrigerant at the distal end of the tip cavity will tend to be converted into a laminar one as the velocity of the vapor increases towards the proximal end of the insert.

The catheter 400 is illustrated as having a closed tip formed by an end cap 475 machined from metal so as to have a relatively thick thermally conductive wall 424 against which the cooling flow is urged. The insert 406 defines an expansion chamber 403 at the refrigerant nozzle or outlet, and the fluid flow provides enhanced thermal contact to the inner wall proximally thereof, so that the entire tip is effectively cooled.

FIG. 9B shows a similar flow conditioning body 506 positioned in the tip of a cryocatheter 500. Catheter 500 has a drawn or spun tip 575, with a wall 524 formed of a sheet of material having a substantially uniform thickness. In this case the interior of the expansion chamber 503 may be enlarged, and a larger flow conditioning body 506 directs the expanding refrigerant against a tip interior wall of larger surface area, permitting an increased cooling capacity. In both configurations, the position of greatest diameter of the body 406 or 506 may be seen to produce an annular venturi-like tapered flow passage extending between the distal refrigerant expansion chamber and the refrigerant return opening of the catheter shaft. In the embodiment of FIG. 9B, a second such tapering passage may be formed between the inner curving shoulder 508 of the formed tip assembly and the proximal surface of the insert body 506.

The invention further contemplates that in addition to enhancing control of the cooling operation of the catheter, a catheter may include a means for warming or thawing of tissue that has been cooled. For this purpose a warming fluid is supplied to the catheter tip.

In general, applicant contemplates that the warming fluid is supplied following the application of cryogenic treatment, and thus is applied in a distinct time interval separate from the application of cold. This will generally be affected by a controller which operates under programmed or push button control, using basic components or switching regimens similar to ones of a known type to control the various elements which will be described further below.

By way of brief overview, in one embodiment, the catheter may be configured to heat the inlet tube, for example, by use of an electrical heater within the catheter body or tip region so that the fluid supplied therethrough warms, rather than cools, the catheter tip area before returning to the catheter handle. In other embodiments, a separate warming fluid supply tube or sub-lumen is provided to carry a distinct warming fluid having characteristics different from the coolant, and better suited to a warming function, for circulation through the catheter tip. For example, a heat transfer fluid may be employed which remains liquid at non-cryogenic or at biological temperature. In each case the existing vacuum return line may serve as the return path for the fluid which has entered the catheter tip. Alternatively, the return lumen may be formed of or partitioned into several paths to separately effect circulation of the two fluids. In another embodiment when a separate warming fluid inlet lumen or line is provided, the invention may further include a switching valve in the region of the handle for interconnecting the warming supply line to the vacuum return port during time intervals when warming fluid is not needed at the tip region. This causes the additional fluid line to serve as an additional return line, thus increasing the circulation rate or capacity during operation of the cooling cycle in addition to providing a separate warming fluid during the warming cycles.

The catheter 50 (FIG. 6A) may also be implemented as a linear cryocatheter, with the internal warming fluid chamber formed by a thin plastic membrane that is effective to warm a non-inflating cooling tip, such as a metal-wrapped cylindrical catheter tip.

FIG. 6 illustrates a construction for providing warming fluid to another embodiment of a cryocatheter in accordance with the invention, configured as an angioplasty balloon catheter designed for physical enlargement of and thermal treatment of the interior of a vessel. In this case, the temperature controlled chamber at the catheter end is an expansion balloon 6000 provided with a partition that is preferably flexible and takes the form of a separating membrane 30 positioned along the path between the warming fluid inlet 6100 and the vacuum outlet 6200, forcing the fluid to circulate from one side to the other of the treatment chamber 6000. The refrigerant injection tube 1 may enter centrally to introduce a flow which is guided by the adjacent membrane 30 and cools the whole chamber as described above; the warming fluid may be provided to the tip via a sector of the main body lumen 1 that extends to the tip region. In a non-inflatable or linear cryotip (FIG. 2, for example), applicant also contemplated a construction that restricts all circulation to a partial cross-section of the chamber. Thus, for example, for a catheter tip of cylindrical cross-section as shown in FIG. 6B, a dividing plate or membrane 13a may entirely separate the interior into a closed chamber 13, and an expansion/return chamber 14. In this case, the supply nozzle 2 opens into the chamber 14, and coolant circulates along its length to the return passage in the catheter body. The other chamber 13 remains empty, and defines a thermally insulating buffer extending along one side of the chamber. The membrane 13a need not be straight, but may be curved as in the axial flow-divider constructions of FIGS. 3A–3C.

FIG. 6A illustrates a further embodiment 50 suitable for both cooling and warming a restenosis catheter. As shown in FIG. 6A, a double balloon layer is formed in the active balloon expansion region, with the inner balloon 51 fed by the coolant injection tube 1 so that, as indicated in phantom, it is urged outwardly against the wall of the catheter when coolant flows from the nozzle 2. The proximal end 51a of the inner balloon opens to allow coolant to pass directly to the vacuum return passage. When the coolant flow is discontinued, the balloon shrinks, and a separate space 3' is formed between the outer wall and the inner balloon, to which warming fluid is fed and may circulate when the coolant pressure at the center has fallen, i.e., during the period at the end of a cooling cycle. In this way the balloon forms a membrane partition that urges the warming fluid toward the surrounding peripheral region but does not interfere with coolant heat transfer during the cooling cycle. As before, a dividing plate or partition may be positioned within the catheter body to limit the warming or cooling effect to one side or the other. Preferably, however, when used for a restenosis balloon, the device is a symmetric balloon body formed of elastomeric material and adapted to heat or cool uniformly around its whole circumference when inflated by fluid for angioplasty operation.

While the invention has been described and illustrated with several basic representations of the chamber, passage and return line configurations contemplated by applicant, it will be understood that in general each of the described catheters may further include one or more sensors, electrodes and control elements of conventional type, such as steering elements, temperature sensing elements and additional lumens for sampling blood gases, enzymes or other material at the catheter tip. Furthermore the elements of construction may include any conventional form of catheter wall, tip movement mechanism, steering wiggler and other elements, such as stiffening, torquing, tensioning or spring wrapped strengthening members of the type known in the art for deployment or use in the construction and design of movable catheter tip assemblies. Mapping electrodes and other signal emitting or receiving electrodes may also be incorporated in the tip structure.

As shown schematically in FIG. 7, one particularly advantageous embodiment of the invention includes an orientation-sensing system 200 for determining the tissue contacting side of the catheter tip. As shown, a series of at least two sensing elements 201a and 201b are positioned at fixed intervals around the tip circumference, and are connected via leads 7000 in the catheter body to a processor/display unit 202.

In one embodiment of this aspect of the invention, the elements 201a and 201b may be a pair of temperature sensors disposed on opposite sides of the tip. The processor/display 202 senses the difference in sensed temperature to determine which side of the tip lies in contact with adjacent tissue. The catheter assembly itself may be configured with a single-plane steering wire to bend toward or away from tissue in the plane of the two sensors. When the tip is equipped with a partition P as shown defining colder and less cold sides of the tip structure, the display may further indicate whether the active side of the tip is urged toward or away from tissue contact. In another embodiment, the sensors 201a and 201b may be implemented as impedance monitoring or signal emitting electrodes. In that case they may operate in conjunction with a body electrode so that the processor/display 202 may compare signal strength of the electrodes 201a and 201b to determine which side of the tip resides in contact with tissue. Alternatively, the electrodes may carry high frequency signals of two different frequencies and the processor may simply detect which of the two frequencies predominates in the signal that has been transmitted through tissue. More than two such electrodes may be provided, and the unit 202 may also employ other detection criteria, such as differential sensing between several of the electrodes on the tip to detect local impedance changes indicative of presence of blood, tissue boundaries or other such features, using this information to distinguish the tip contact orientation.

In addition to balloon-type dividers as shown in FIGS. 6 and 6A, the invention contemplates membrane divider constructions applicable to diverse warming tip implementations. FIG. 8 shows a sectional end view, taken midway along the length of a catheter tip 300 in one such embodiment. As shown, the cooling injection tube 1 enters the tip 300 centrally, and a separating plate or membrane 310 divides the cooling chamber 3 into two half-chambers (8000a and 8000b respectively) extending back to the main body of the catheter. A second plate or membrane 311, which may be a thin film flexibly biased against the plate 310 so that it spreads apart only when warming fluid is injected between the walls 310, 311, provides warming fluid manifolds (8100a and 8100b respectively) that fill the thermal contact portion of the tip and channels warming fluid back toward the return passage. This manifold may be provided with warming fluid, in turn, via a separate supply tube extending from the handle through the catheter body, or the catheter body itself may be subdivided by one or more septa to provide one or more isolated sectors of its cross-sectional flow path dedicated to the supply of warming fluid to the tip.

The invention being thus disclosed and described, further variations and modifications will occur those skilled in the art, and all such variations and modifications are considered to be within the spirit and scope of the invention, as defined by the claims appended hereto and equivalents thereof.

What is claimed is:

1. A cryocatheter for the cryotreatment of tissue, such cryocatheter comprising:
   a coolant line
   a cryochamber having a coolant receiving interior and a thermally conductive wall for contacting and conductively treating tissue in contact with said wall, said cryochamber receiving coolant from the coolant line
   a return line for return of spent coolant, and
   a flow directing body in said cryochamber effective to condition and direct a flow of coolant through the cryochamber from said coolant line to said return line, the flow directing body providing a defined path for coolant flow substantially throughout the cryochamber so as to more effectively cool said thermally conductive wall of said cryochamber.

2. The cryocatheter of claim 1, wherein said flow directing body is a partition that extends axially from the outlet of the coolant line substantially into the cryochamber to define an elongated sub-chamber of said cryochamber which is preferentially cooled.

3. The cryocatheter of claim 2, wherein said partition extends to channel the coolant from a central region outwardly against the peripheral wall of the cryochamber.

4. The cryocatheter of claim 2, wherein said partition isolates a side of said chamber to form an uncooled buffer region.

5. The cryocatheter of claim 1, wherein said return line is a vacuum return line.

6. The cryocatheter of claim 1, further comprising means for warming said cryochamber tip to accelerate thawing of treated tissue.

7. The cryocatheter of claim 6, wherein said means for warming includes a heater in thermal contact with a fluid supply line.

8. The cryocatheter of claim 7, wherein said fluid supply line is the coolant line.

9. The cryocatheter of claim 7, wherein said fluid supply line is a warming fluid supply line distinct from the coolant line.

10. The cryocatheter of claim 9, further comprising a switched valve for connecting said warming line as an additional return line during application of coolant to the cryochamber, and connecting said warming line as a fluid supply line during warming of treated tissue.

11. The cryocatheter of claim 1, further comprising sensing means for sensing contact orientation of the catheter against adjacent tissue.

12. A cryocatheter for the cryotreatment of tissue, such cryocatheter comprising:
   a coolant line
   a cryochamber having a coolant receiving interior and a thermally conductive wall for contacting and conductively treating tissue in contact with said wall, said cryochamber receiving coolant from the coolant line
   a return line for return of spent coolant, and
   a body in said cryochamber effective to condition flow of coolant from said coolant line to said return line so as to more effectively cool said wall portion, wherein said body is a partition that extends axially to define an elongated sub-chamber of said cryochamber, said partition blocking circulation of coolant along a side of the cryochamber to define an uncooled side of the cryochamber.

13. A cryocatheter for the cryotreatment of tissue, such cryocatheter comprising:
   a coolant line
   a cryochamber having a coolant receiving interior and a thermally conductive wall for contacting and conductively treating tissue in contact with said wall, said cryochamber receiving coolant from the coolant line
   a return line for return of spent coolant
   a body in said cryochamber effective to condition flow of coolant from the coolant line to said return line so as to more effectively cool said wall portion, wherein said body is a partition that extends axially to define said sub-chamber extending along a segmented length around a partial circumference of the cryochamber.

14. A cryocatheter for the cryotreatment of tissue, such cryocatheter comprising:
   a coolant line
   a cryochamber having a coolant receiving interior and a thermally conductive wall for contacting and conductively treating tissue in contact with said wall, said cryochamber receiving coolant from the coolant line
   a return line for return of spent coolant
   a body in said cryochamber effective to condition flow of coolant from the coolant line to said return line so as to more effectively cool said wall portion, and
   a sensing means for sensing contact orientation of the catheter against adjacent tissue, the sensing means including a first impedance monitoring electrode on a first side of the cryochamber, and a second impedance monitoring electrode on a second side of the cryochamber, said first and second impedance monitoring electrodes being effective to define a determinable sensing path when one side of the cryochamber contacts tissue.

15. The cryocatheter of claim 14, wherein said first and second electrodes are operable to conduct signals of first and second frequencies for distinguishing the tissue contacting wall of the cryochamber.

16. A cryocatheter for the cryotreatment of tissue, such cryocatheter comprising:
   a coolant line
   a cryochamber having a coolant receiving interior and a thermally conductive wall for contacting and conductively treating tissue in contact with said wall, said cryochamber receiving coolant from the coolant line
   a return line for return of spent coolant
   a body in said cryochamber effective to condition flow of coolant from the coolant line to said return line so as to more effectively cool said wall portion, and
   a sensing means for sensing contact orientation of the catheter against adjacent tissue, the sensing means including a first temperature sensor on one side of the cryochamber and a second temperature sensor on another side of the cryochamber, said temperature sensors being connected through the catheter to show a differential temperature indicative of tip contact orientation.

17. A cryocatheter for the cryotreatment of tissue, the cryocatheter comprising:
   a first distal end portion;
   an injection lumen, the injection lumen having a second distal end portion and supplying coolant to the first distal end portion;

a cryochamber in the first distal end portion, the cryochamber being in fluid communication with and substantially enclosing the second distal end portion of the injection lumen, the cryochamber having:
  a first thermally conductive interior surface in operative contact with the coolant; and
  a second thermally conductive exterior surface for contacting tissue;
a return lumen in fluid communication with the cryochamber for return of spent coolant;
a flow directing body in the cryochamber, the flow directing body defining a surface; and
a coolant receiving interior volume defined by the first thermally conductive interior surface of the cryochamber and the surface of the flow directing body, the coolant receiving interior volume being effective to provide a defined volume for coolant flow substantially throughout the cryochamber.

18. The cryocatheter of claim 17, wherein said flow directing body is an annular body having:
  a central lumen circumferentially enclosing and coupled to the injection lumen; and
  a smoothly curved axially distal surface portion; and
  a smoothly tapered axially proximal surface portion, the proximal surface portion being coupled to the smoothly curved distal surface portion.

19. The cryocatheter of claim 17, wherein the flow directing body is axially positioned at predetermined positions along the length of the second distal end portion of the injection lumen, the flow directing body providing defined volumes for coolant flow substantially throughout the cryochamber.

* * * * *